(12) United States Patent
Lewis et al.

(10) Patent No.: US 12,098,220 B2
(45) Date of Patent: Sep. 24, 2024

(54) RADIOPAQUE POLYMERS

(71) Applicant: BIOCOMPATIBLES UK LIMITED, Farnham (GB)

(72) Inventors: Andrew Lennard Lewis, Farnham (GB); Jasmine Lord, Dronfield (GB)

(73) Assignee: Boston Scientific Medical Device Limited, Galway (IE)

( * ) Notice: Subject to any disclaimer, the term of this patent is extended or adjusted under 35 U.S.C. 154(b) by 31 days.

(21) Appl. No.: 17/252,564

(22) PCT Filed: Jun. 26, 2019

(86) PCT No.: PCT/IB2019/055394
§ 371 (c)(1),
(2) Date: Dec. 15, 2020

(87) PCT Pub. No.: WO2020/003153
PCT Pub. Date: Jan. 2, 2020

(65) Prior Publication Data
US 2021/0221928 A1 Jul. 22, 2021

(30) Foreign Application Priority Data
Jun. 29, 2018 (GB) ..................... 1810784

(51) Int. Cl.
*C08F 12/16* (2006.01)
*A61B 17/12* (2006.01)
(Continued)

(52) U.S. Cl.
CPC ........ *C08F 12/16* (2013.01); *A61B 17/12181* (2013.01); *A61B 17/12186* (2013.01);
(Continued)

(58) Field of Classification Search
CPC ...... C08F 12/22; C08F 112/22; C08F 212/22; C08F 12/16; C08F 112/16; C08F 212/16;
(Continued)

(56) References Cited

U.S. PATENT DOCUMENTS 4,350,773 A 9/1982 Itagaki et al.
2015/0110722 A1* 4/2015 Hohn ................. A61K 49/0457
424/9.44

FOREIGN PATENT DOCUMENTS

CN 101513542 A 8/2009
EP 2365009 A1 * 9/2011 ......... A61K 49/0442
(Continued)

OTHER PUBLICATIONS

Raissi et al., "Upper Gastrointestinal Bleed Embolizationwith Onyx: The ""Tattoo Effect" 2018 Journal of Clinical Imaging Science—4 pages.
(Continued)

*Primary Examiner* — Ling Siu Choi
*Assistant Examiner* — David L Miller
(74) *Attorney, Agent, or Firm* — Seager, Tufte & Wickhem, LLP

(57) ABSTRACT

A liquid composition comprising a polymer having pendant groups of the formula I: (I) Wherein X is either a bond or is
(Continued)

a linking group having 1 to 8 carbons and optionally 1 to 4 heteroatoms selected from O, N and S; and n is 1 to 4.

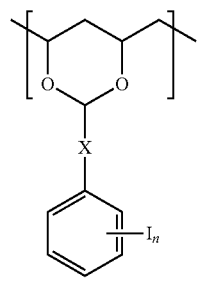

(I)

14 Claims, 8 Drawing Sheets

(51) Int. Cl.
| | |
|---|---|
| *A61K 49/04* | (2006.01) |
| *C08F 12/22* | (2006.01) |
| *C08F 112/14* | (2006.01) |
| *C08F 116/06* | (2006.01) |
| *C08F 212/14* | (2006.01) |
| *C08F 16/06* | (2006.01) |
| *C08F 16/38* | (2006.01) |
| *C08F 116/38* | (2006.01) |
| *C08F 216/06* | (2006.01) |
| *C08F 216/38* | (2006.01) |

(52) U.S. Cl.
CPC ...... *A61K 49/0442* (2013.01); *A61K 49/0452* (2013.01); *C08F 12/22* (2013.01); *C08F 112/16* (2020.02); *C08F 112/22* (2020.02); *C08F 116/06* (2013.01); *C08F 212/16* (2020.02); *C08F 212/22* (2020.02); *C08F 16/06* (2013.01); *C08F 16/38* (2013.01); *C08F 116/38* (2013.01); *C08F 216/06* (2013.01); *C08F 216/38* (2013.01)

(58) Field of Classification Search
CPC ...... C08F 16/06; C08F 116/06; C08F 216/06; C08F 216/38; C08F 16/38; C08F 116/38; A61B 17/12181; A61B 17/12186; A61K 49/0442; A61K 49/0452
See application file for complete search history.

(56) References Cited

FOREIGN PATENT DOCUMENTS

| | | |
|---|---|---|
| JP | 2013521087 A | 6/2013 |
| WO | 2011110589 A1 | 9/2011 |
| WO | 2015033093 A1 | 3/2015 |
| WO | WO-2015033092 A1 * | 3/2015 ........... A61K 31/404 |
| WO | 2017037276 A1 | 3/2017 |

OTHER PUBLICATIONS

International Search Report and Written Opinion for the International Patent Application No. PCT/IB2019/055394, mailed Nov. 25, 2019, 11 pages.

Oliver Dudeck: "Intrinsically radiopaque iodine-containing polyvinyl alcohol as a liquid embolic agent: evaluation in experimental wide-necked aneurysms", Journal of Neurosurgery, vol. 104, No. 2, Jan. 1, 2006, pp. 290-297.

* cited by examiner

A                              B                              C

RADIOPAQUE POLYMERS

CROSS-REFERENCE TO RELATED APPLICATION

This is the United States National Phase entry of International Application No. PCT/IB2019/055394, filed Jun. 26, 2019, which claims priority to Great Britain Application No. 1810784.7, filed Jun. 29, 2018, the disclosures of which are incorporated herein by reference in their entireties.

This invention relates to radiopaque polymers and to their use as liquid embolics useful in the field of therapeutic embolisation.

Therapeutic embolisation is a minimally invasive procedure in which a material is introduced into a blood vessel to produce an occlusion in order to slow or stop blood flow. Typically such materials are delivered via a microcatheter, which is navigated to the target site from a peripheral point such as the leg or wrist. This approach has been useful in the treatment of conditions such as gastrointestinal bleeding, arteriovenous malformations, hypervascular malignant tumours such as hepatocellular carcinoma, benign growths such as uterine fibroids and more recently benign prostate hyperplasia (BPH) amongst others.

Biocompatible microspheres are useful embolic agents because they can be easily delivered to the target site and can be provided in defined size ranges for more predictable embolisation according to the vessel size. Liquid embolic formulations have also been prepared, where a composition is delivered to the target site within the body as a liquid, but forms an embolus in a blood vessel in vivo, particularly where the polymer gels, solidifies or precipitates in situ to form the embolus.

Some such systems rely on polymer formation or gelling in situ, whilst others rely on delivery in organic solvents, which rapidly dissipate in the blood leaving behind the embolic material. Liquid embolics have the added advantage that they conform to the vessel wall and, depending on their deposition characteristics, typically form a unified embolus, rather than discrete spheres.

Liquid embolic compositions should be biocompatible, and have appropriate density, compressibility, flowability and ease of catheter delivery. Flow characteristics within the vessel, speed and predictability of deposition and robustness of the embolus are also important.

Radiopaque polymer microspheres having iodinated groups covalently coupled to the polymer backbone have been proposed (e.g. WO2015/033092). Radiopaque liquid embolics having iodinated groups coupled to the polymer backbone have also been described (e.g. WO2011/110589). It is desirable to provide improved iodinated polymers that are sufficiently radiopaque to be visible on X-ray, but have improved usability properties.

The present inventors have identified that one or more of these issues can be addressed by the polymers and compositions described herein.

Thus in a first aspect, the invention provides

A liquid composition comprising a polymer having pendant groups of the formula I.

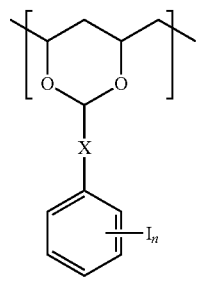

Wherein X is either a bond or is a linking group having 1 to 8 carbons and optionally 1 to 4 heteroatoms selected from O, N and S; and n is 1 to 4; preferably 2 or 3.

The polymer having pendant groups of the formula 1 may be any polymer comprising repeating 1,3 diol groups. In these polymers the iodinated phenyl group may be coupled by reaction with a aldehyde, acetal or semi acetal group to form the 1,3 dioxalone ring. Preferably the polymer is a vinylalcohol polymer such as poly(vinylalcohol) or (ethylene-vinylalcohol) polymers or co-polymers; Particularly the polymer is a polyvinyl alcohol (PVA) homo-polymer or co-polymer.

The polymer is preferably non cross linked.

The native PVA polymer may be acetylated or non acetylated, typically the level of acetylation in the native PVA is between 50% and 100%, preferably 80% to 100%.

PVAs suitable for use in the invention have a weight average molecular weight ranging from 1 KDa to 250 kDa, preferably however the PVA has a weight average molecular weight of at least 20 kDa and preferably at least 40 kDa. Preferred ranges include 40 to 250 kDa and 40 to 200 kDa.

X is preferably either a bond or is a linking group having 1 to 4 carbons and optionally 1 heteroatom selected from O and N; and is more preferably selected from a bond, $(C_{1-4})$ alkylene, $(C_{1-4})$oxyalkylene, amino$(C_{1-4})$alkylene. Particular examples include a bond, $C_1$, $C_2$ or $C_3$ alkylene, oxymethyl or oxyethyl, aminomethylene and aminoethylene. Where a linker is present it is particularly a methylene, oxymethylene or amino methylene. Most preferably the ring is directly bonded to the group G, such that X is a bond.

The pendant group of the formula I may comprise 1, 2, 3 or 4 iodines covalently attached to the ring. Preferably however the pendant group comprises 2 or 3 iodines. Preferred arrangements include:

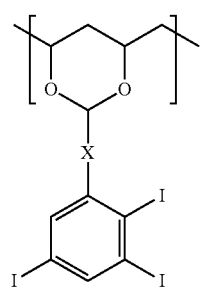

-continued

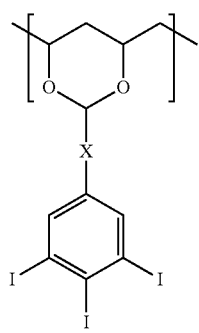

2b

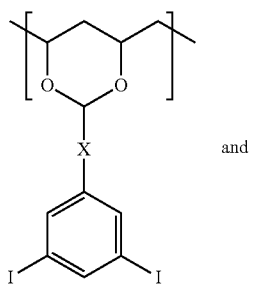
and

2c

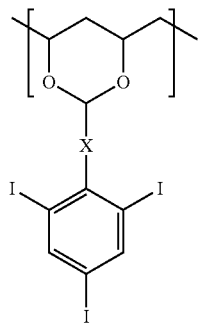

2d

The most preferred pendant group is a group of the formula 3:

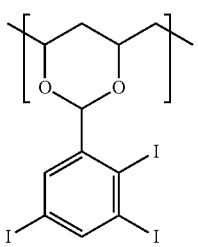

3

The invention also provides, in a second aspect, a non cross linked polyvinyl alcohol homopolymer having pendant groups of the formula I:

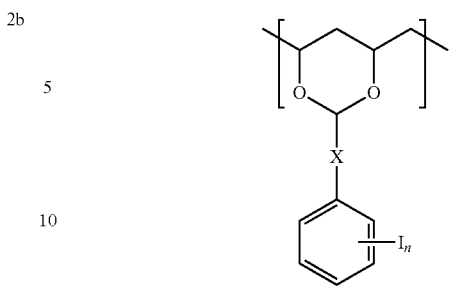

3

Wherein X is either a bond or is a linking group having 1 to 8 carbons and optionally 1 to 4 heteroatoms selected from O, N and S; and n is 1 to 4.

In one embodiment, the polymer comprises 2 or more versions of the pendant groups of formula 1, each varying from the other in the value for n. There may for example be 2, 3, 4 or more such pendant groups each having a different value for n For example the polymer may comprise pendant groups having 3 iodines and pendant groups having 1 iodine, or pendant groups having 4 iodines and pendant groups having 1 iodine or pendant groups having 2 iodines and pendant groups having 3 iodines, or pendant groups having 1 iodine, pendant groups having 2 iodines and pendant groups having 3 iodines. The proportion of each group may be varied to suit the required properties. In this way the overall hydrophobicity and iodine content/radiodensity of the polymer can be fine-tuned to improve the physical properties such as precipitation, solubility, density robustness of the precipitate.

The proportion of one iodination value to another can be achieved either by providing a suitable ratio of iodinated phenyl moieties having the appropriate ratio if n values as starting materials, or by mixing polymers having pendant groups with different n values in the appropriate proportion.

The polymer may be biodegradable. Biodegradable polymers have linkages that are cleaved by hydrolysis within the body, such that the polymer breaks down. To provide biodegradability, polymers may be provided with a linkage in the polymer backbone that is hydrolytically cleaveable in the human body, such as an ester group. The preferred polymers degrade to soluble components over a period of 1 hour to 1 year. Alternatively the polymer may be non biodegradable, such that it will remain present within the body in a stable form for a period greater than 1 year.

Liquid embolic compositions are compositions where the polymer is delivered to the desired site within the body as a liquid, but forms an embolus in a blood vessel in vivo, particularly where the polymer gels, solidifies or precipitates in situ to form the embolus. Such compositions typically comprise polymers as described herein and a solvent, which may be an aqueous or organic solvent. Preferably the composition comprises a polymer of the formula 1 completely dissolved in the solvent to form a solution of the polymer in the solvent.

Radiopacity, or radiodensity, may be varied as required by adjusting the amount of iodine in the polymer. This can be achieved by varying the number of iodines on the ring or by varying the proportion of pendant group to polymer.

The polymers of the invention preferably have at least 0.1 eq. of pendant groups measured as 1 pendant group to 2 hydroxyls of the polymer backbone. Preferably polymers have at least 0.4 eq. most preferably at least 0.6 eq. pendant groups, particularly where the pendant group carries 3 iodines.

The quantity of iodine in the polymer is preferably at least 10, preferably at least 30, more preferably at least 40 and most preferably at least 50% wt/wt polymer by dry weight. High radiodensity in these polymers can be obtained where iodine is greater than 40% wt/wt dry polymer.

Preferably the polymer of the invention has a radiodensity of at least 1000 preferably at least 2000 more preferably at least 3000 and particularly at least 4000 HU. When measured at 65 kV, especially as measured according to Example 7.

Compositions of the invention, intended to precipitate at the target site within the body, typically precipitate in contact with normal saline at 20° C. and compositions in which the polymer precipitates under these conditions provide a further embodiment of the invention. The radiodensity and iodine content of these precipitates is preferably within the ranges preferred for other embodiments of the invention.

In one approach, polymers described herein may be provided as a solution in an organic solvent. Typically such solvents are miscible with water. By water miscible is meant that 0.5 ml of the solvent is completely soluble in 1 litre of normal saline at 20° C.

Preferably these solvents are biocompatible. Preferably the solvents are polar aprotic solvents. Preferred solvents are Dimethyl sulfoxide (DMSO), Dimethylformamide (DMF), DMPU (N, N'-dimethylpropyleneurea), DMI (1,3-dimethyl-2-imidazolidinone), glycerol, ethyl lactate, N-Methyl-2-pyrrolidone (NMP) and glycofurol (2-(Oxolan-2-ylmethoxy) ethanol). The solvents are preferably selected from DMSO and NMP.

In one embodiment, the organic solvent may comprise up to 50% water, preferably up to 25% and most preferably up to 10%.

In one preferred embodiment the aqueous solvent includes a pharmaceutically acceptable buffer. Examples of such buffers include phosphate, citrate, tromethamine and acetate.

Preferably the liquid composition comprises between 3% and 70% wt/wt, preferably at least 20%. Compositions of 5% to 40%, dissolved polymer or 5% to 25% have useful properties.

The liquid embolic compositions optionally further comprise an active agent. A proportion of the active agent becomes trapped within the polymer as it precipitates and is then released over a period of time. This approach is particularly useful in more hydrophobic drugs since these precipitate with the polymer and so more is trapped.

The active agent may be a chemotherapeutic agent, an antibody such as cetuximab, trastuzimab and nivolumab, an antibody fragment, a peptide, a low molecular weight protein, or a combination thereof.

Exemplary chemotherapeutic agents include the anthracycline class such as but not limited to doxorubicin, daunarubicin, epirubicin and idarubicin; the camptothecin class such as but not limited to irinotecan, topotecan, and exatecan; the platins such as cisplatin, oxaliplatin, carboplatin and miriplatin; mitomycin C, antimetablites such as 5-fluorouracil; multityrosine kinase inhibitors such as but not limited to sorafenib, sunitinib, regorafenib, brivinb, dasetanib, bosutinib, erlotinib, gefitinib, imatinib and vandetinib, rapamycin or any combination thereof.

A further aspect of the present invention provides methods of medical treatment comprising delivering a liquid embolic composition comprising a polymer of the formula I as described herein, to a blood vessel of a subject in need thereof, such as to form an embolus.

The polymer may be delivered in the form of a composition comprising a solvent that dissipates in the blood stream to provide an embolus, typically an organic solvent as described above.

In a further embodiment, the present invention also provides pharmaceutically active ingredients as described herein, for use in a method of medical treatment, wherein the treatment comprises delivering the pharmaceutical active to the patient in the form of an embolic composition comprising the active as described herein and from which the active is eluted during the treatment.

Liquid embolics described herein may be used to treat a variety of conditions including arteriovenous malformations, gastrointestinal bleeding, filling of aneurysms, treatment of solid tumours, particularly hypervascular tumours, such as those of the liver, prostate, kidney, brain, colon, bone and lung. As well as benign hyperplastic conditions such as prostate hyperplasia or uterine fibroids. The approach can also be used in the treatment of obesity and joint pain.

FIGURES

Figure 8:
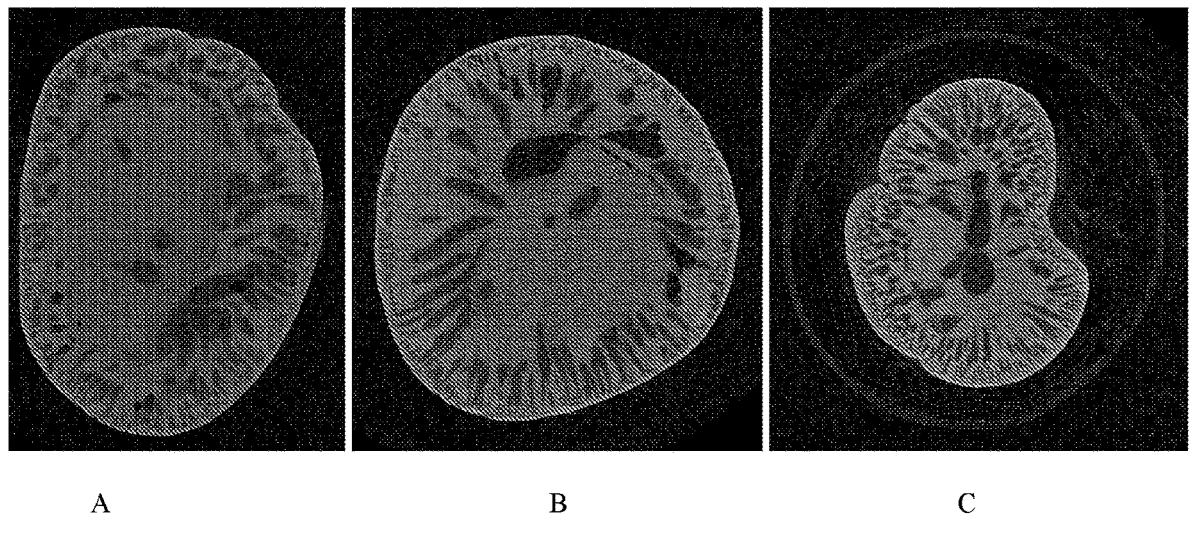

FIG. 8 shows microCT images of precipitated liquid embolic polymers prepared with 0.10 (A) 0.15 (B) and 0.20 (C) eq. TIBA The invention will now be described further by way of the following non limiting examples with reference to the figures. These are provided for the purpose of illustration only and other examples falling within the scope of the claims will occur to those skilled in the art in the light of these. All references cited herein are incorporated by reference in their entirety. Any conflict between that reference and this application shall be governed by this application.

EXAMPLES

Example 1: General Liquid Embolic Synthesis Conditions

To a pre-dried reactor under a nitrogen blanket was added PVA (typically 5-10 g) and anhydrous solvent (typically DMSO or NMP, 40 vol w.r.t. PVA mass) and catalyst (typically 2.2 vol w.r.t. PVA mass). The stirred suspension was heated to elevated temperature (ca 90° C.) to dissolve the PVA. When a homogeneous solution had been obtained, the mixture was cooled to the desired reaction temperature (typically 50-80° C.). 2,3,5 Triiodo benzaldehyde (TIBA—typically 0.1 to 0.6 eq w.r.t. PVA diol functionalities) was added. The reaction was then stirred under an $N_2$ blanket and the reaction conversion was monitored by High Performance Liquid Chromatography (HPLC) for consumption of TIBA. At a pre-determined time (typically when consumption of the chemical substrate had ceased) an anti-solvent was added (typically, acetone, Dichloromethane (DCM), Acetonitrile (MeCN) or Methyl tert-butyl ether (TBME), ca 40 vol) dropwise from a dropping funnel. The supernatant fluid was removed by aspiration through a filter membrane and further reaction solvent (typically 40 vol) was charged and stirred until the solids had fully dissolved. This solvent washing stage was repeated up to 3 times. Then the solid was re-dissolved in reaction solvent, and precipitated by the slow addition of water (typically up to 100 vol). The resulting aggregated solid was removed from the supepatant and homogenised in a blender in water (Ca 1l). The suspension was filtered and re-suspended in water (typically 100 vol) and slurried for up to 30 minutes and filtered. The water slurrying was repeated until pH neutral had been obtained, then the damp solids were slurried in acetone (100 vol, 30 mins stir, 2 repetitions), filtered and dried in a high vacuum oven at 30° C. for up to 24 h. Table 1 shows iodine content of liquid embolic preparations.

TABLE 1

| Prep. | MW PVA | Conditions | Eq TIBA | Conversion | Isolated Yield | % $I_2$ (w/w) |
|---|---|---|---|---|---|---|
| 1 | 9-10 kDa* | DMSO, 60° C. | 0.01 eq | 100% | Water sol. | N/A |
| 2 | 67 kDa** | DMSO, 60° C. | 0.07 eq | 100% | 78.8% | 27.9% |
| 3 | 67 kDa** | DMSO, 60° C. | 0.06 eq | ND | 82.9% | 18.0% |
| 4 | 67 kDa** | DMSO, 60° C. | 0.03 eq | ND | 59.4% | 12.0% |
| 5 | 67 kDa** | DMSO, 60° C. | 0.4 eq | 91% | 80.7% | 55.1% |
| 6 | 67 kDa** | DMSO, 60° C. | 0.6 eq | 76% | 79.9 | 60.1% |
| 7 | 146-186 kDa*** | DMSO, 65° C. | 0.1 eq | 100% | 84.7% | 30.5% |
| 8 | 146-186 kDa*** | DMSO, 65° C. | 0.25 eq | 99.9% | 92.9% | 47.2 |
| 9 | 146-186 kDa*** | DMSO, 65° C. | 0.4 eq | 99.4% | 94.1% | 55.8% |
| 10 | 85-124 kDa*** | DMSO, 70° C. | 0.1 eq | 100% | 94.7% | 28.8% |
| 11 | 85-124 kDa*** | DMSO, 70° C. | 0.25 eq | 100% | 93.6% | 46.2% |
| 12 | 85-124 kDa*** | DMSO, 70° C. | 0.4 eq | 100% | 91.3% | 55.4% |
| 13 | 85-124 kDa*** | DMSO, 70° C. | 0.6 eq | 99.9% | 89.5% | 62.0% |

Eq. refers to the equivalents relative to free diol units on the PVA backbone.
*= 80% hydrolysed
**= 88% hydrolysed
***= 100% hydrolysed.

Example 2: Formulation of Iodinated PVA Liquid Embolic Prototypes

Prototype formulations were prepared as follows: iodinated PVA prepared according to general example 1, was weighed into a 10 ml vial, to which was added the desired solvent (typically DMSO or NMP) such that the overall concentration was in the range 4-20% w/w with a total volume being less than 10 ml. The vial containing the suspension was then sealed and placed in a sonicator, and sonicated until complete dissolution had occurred (typically ca 4 hours). Table 1 provides example liquid embolic Formulations.

TABLE 2

Example liquid embolic formulations.

| Sample Number | PVA Molecular Weight | TIBA Equivalent | PVA Concentration in DMSO (w/w %) |
|---|---|---|---|
| 1 | 67 kDa | 0.25 | 8 |
| 2 | 67 kDa | 0.25 | 20 |
| 3 | 67 kDa | 0.20 | 20 |
| 4 | 67 kDa | 0.40 | 4 |
| 5 | 67 kDa | 0.40 | 8 |
| 6 | 67 kDa | 0.40 | 12 |
| 7 | 67 kDa | 0.40 | 16 |
| 8 | 67 kDa | 0.60 | 4 |
| 9 | 67 kDa | 0.60 | 8 |
| 10 | 67 kDa | 0.60 | 12 |
| 11 | 67 kDa | 0.60 | 16 |
| 12 | 85-124 kDa | 0.10 | 8 |
| 13 | 85-124 kDa | 0.25 | 8 |
| 14 | 85-124 kDa | 0.40 | 8 |
| 15 | 85-124 kDa | 0.60 | 8 |

TABLE 2-continued

Example liquid embolic formulations.

| Sample Number | PVA Molecular Weight | TIBA Equivalent | PVA Concentration in DMSO (w/w %) |
|---|---|---|---|
| 16 | 146-186 kDa | 0.10 | 4 |
| 17 | 146-186 kDa | 0.10 | 8 |
| 18 | 146-186 kDa | 0.25 | 4 |
| 19 | 146-186 kDa | 0.25 | 8 |

TABLE 2-continued

Example liquid embolic formulations.

| Sample Number | PVA Molecular Weight | TIBA Equivalent | PVA Concentration in DMSO (w/w %) |
|---|---|---|---|
| 20 | 146-186 kDa | 0.40 | 4 |
| 21 | 146-186 kDa | 0.40 | 8 |

Example 3 Precipitate Solidification

Elution of the solvent (DMSO) from the liquid samples was used as a measure of the progress of solidification. Testing was performed in a Sotax USP II dissolution bath connected to a UV spectrophotometer. The dissolution bath was set to 37.5° C. and each vessel filled with 500 mL of phosphate buffered saline (PBS) with stirring at 50 rpm.

Figure 1:
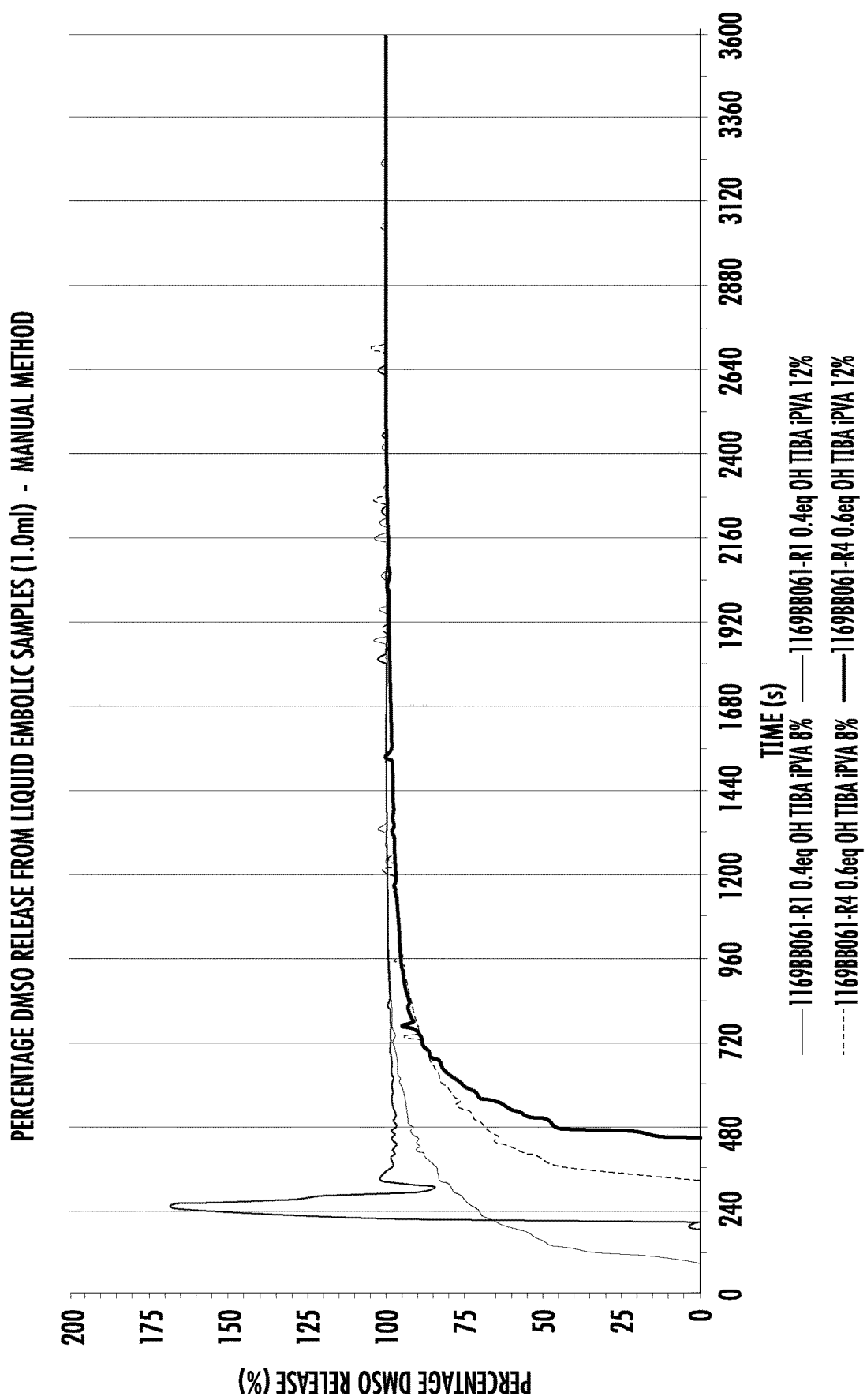
FIG. 1 illustrates the release of DMSO measured by UV absorption at 231 nm, from a selection of liquid embolic formulations of the invention.

The elution of DMSO within the vessel was measured by UV at the wavelength of 231 nm over time (maximum of 2 hours), giving an indication of the rate at which a liquid embolic precipitate is solidifying. 1 ml of the liquid embolic sample was withdrawn using a 3 mL DMSO compatible syringe. This was added, dropwise into the dissolution vessels via the delivery port. At two minute intervals additional samples were added to the remaining Sotax USP II dissolution vessels. Once all samples had been added, the system was left to run for the total measurement run time. At the completion of the measurement run time, the system was stopped and the precipitate was retained for further analysis. The Solidification Time recorded was the point at which 90% of DMSO had been eluted from the precipitate. The percentage of the DMSO eluted from the liquid embolic was based upon the point where the curve had plateaued to remove the influence of the flushes of DMSO observed in samples which precipitate immediately on impact in the PBS (see FIG. 1).

Tables 2a to 2c illustrate the precipitation times for liquid embolic preparations.

TABLE 2a

Precipitation times for low molecular weight preparations

| Sample Number | Radiopaque Group (TIBA) Equivalent | Polymer Concentration in DMSO (%) | Solidification Time (>90%) (mm:ss) |
|---|---|---|---|
| 1 | 0.25 | 8 | 01:37 |
| 2 | 0.25 | 20 | 05:13 |
| 3 | 0.20 | 20 | 05:35 |
| 4 | 0.40 | 4 | 00:17 |
| 5 | 0.40 | 8 | 03:42 |
| 6 | 0.40 | 12 | 05:13 |
| 7 | 0.40 | 16 | 06:07 |
| 8 | 0.60 | 4 | 00:22 |
| 9 | 0.60 | 8 | 03:59 |
| 10 | 0.60 | 12 | 05:42 |
| 11 | 0.60 | 16 | 05:42 |

TABLE 2b

Precipitation times for medium molecular weight preparations

| Sample Number | Radiopaque Group (TIBA) Equivalent | Polymer Concentration in DMSO (%) | Solidification Time (>90%) (mm:ss) |
|---|---|---|---|
| 12 | 0.10 | 8 | 00:22 |
| 13 | 0.25 | 8 | 06:50 |
| 14 | 0.40 | 8 | 09:21 |
| 15 | 0.60 | 8 | 05:24 |

TABLE 2c

Precipitation times for high molecular weight preparations.

| Sample Number | Radiopaque Group (TIBA) Equivalent | Polymer Concentration in DMSO (%) | Solidification Time (>90%) (mm:ss) |
|---|---|---|---|
| 16 | 0.10 | 4 | 00:22 |
| 17 | 0.10 | 8 | Not Performed |
| 18 | 0.25 | 4 | 00:22 |
| 19 | 0.25 | 8 | 09:00 |
| 20 | 0.40 | 4 | 00:22 |
| 21 | 0.40 | 8 | 05:24 |

Figure 3:
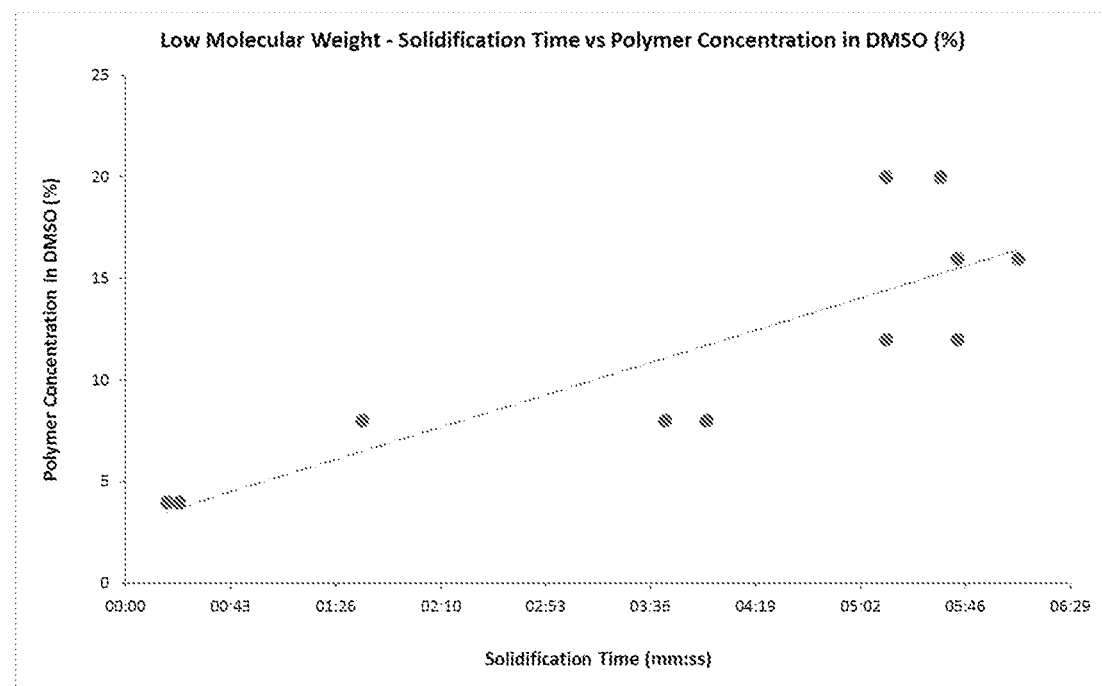
FIG. 3 illustrates the relationship between solidification time and polymer concentration for low molecular weight polymers.

FIG. 3 Illustrates the relationship between solidification time and polymer concentration for low molecular weight polymers.

Example 4: Precipitation Fill Volume

Precipitation fill volume provides a measurement of the percentage reduction in volume of liquid embolic samples after the samples precipitates in PBS and of how much solid precipitate is formed from a known liquid volume.

Figure 2:
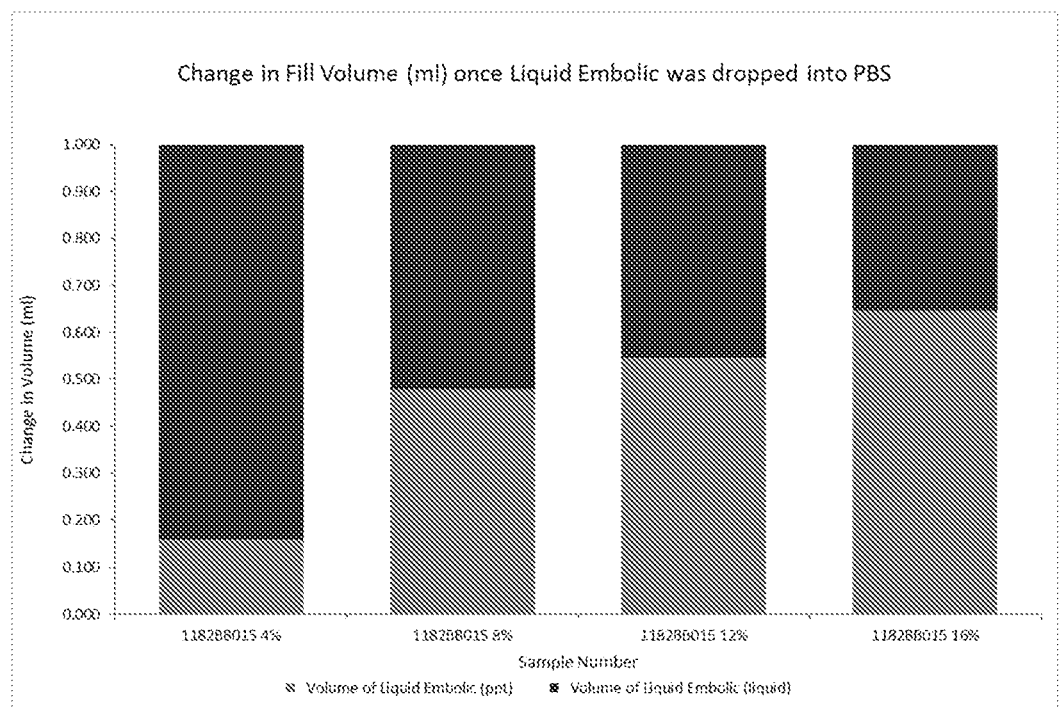
FIG. 2 illustrates the change in Precipitation Fill Volume of Liquid Embolic samples

15 ml of PBS was added to a clean, dry medium sized glass petri dish (approximately 10 cm in diameter) and a known volume of the liquid embolic to be tested (ideally 0.5 ml) was deposited dropwise into the PBS solution and allowed to solidify for 10 minutes. Once the samples had solidified for 10 minutes, the precipitate was removed and air dried on a sheet of filter paper. Precipitate volume was then measured by displacement in PBS. FIG. 2 illustrates volume reduction values of the liquid embolic samples.

Figure 4:
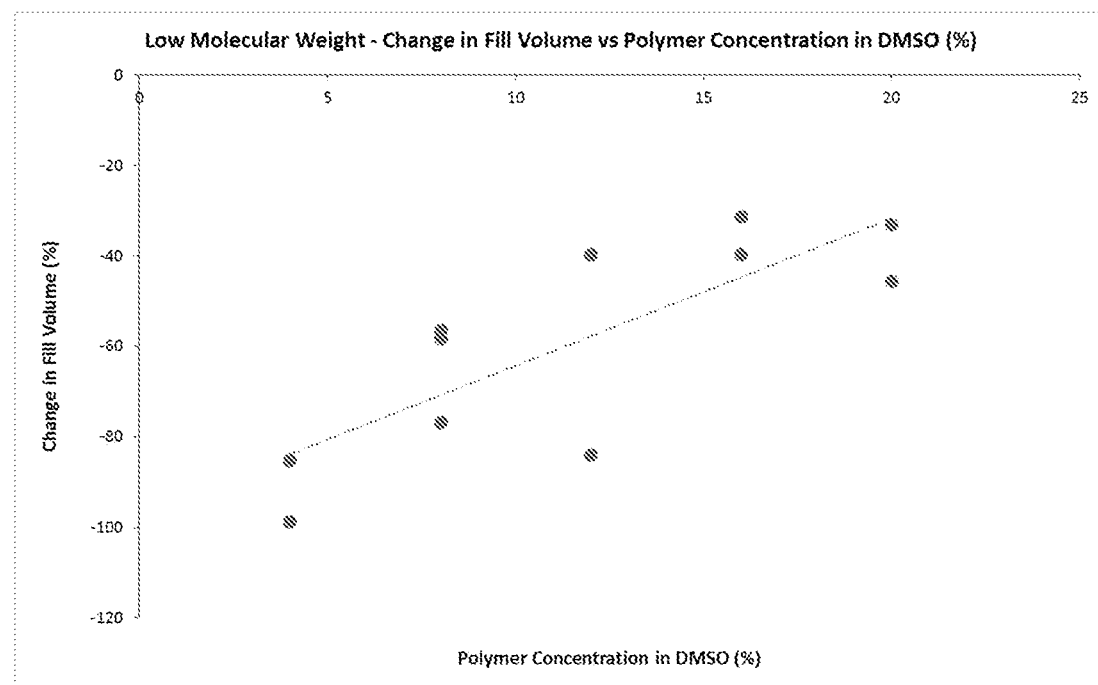
FIG. 4 illustrates the effect of polymer concentration on fill volume.
Figure 5:
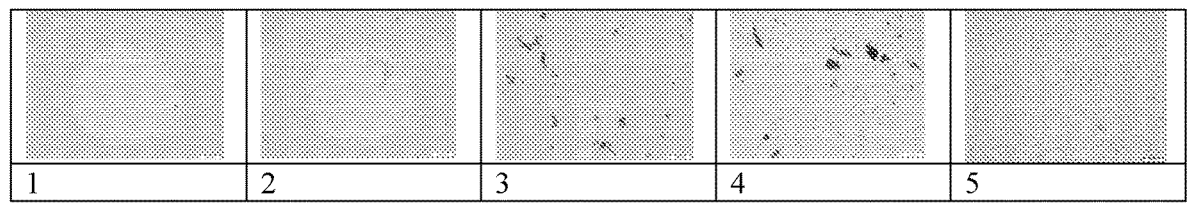
FIG. 5 shows typical particulate formation for score values of 1-5.
Figure 6:
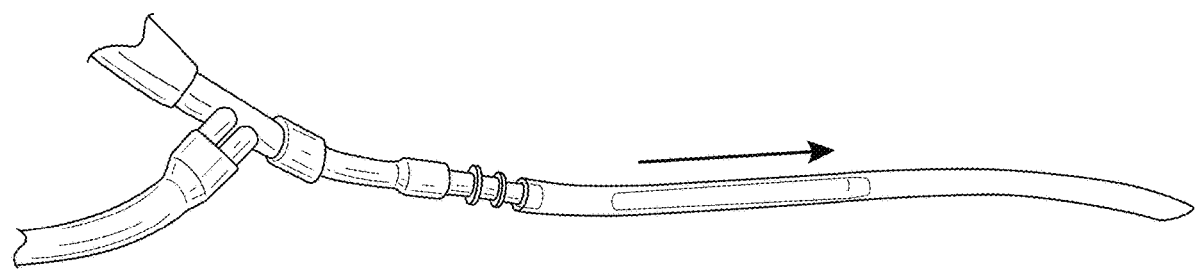
FIG. 6 shows the set up used to observe precipitation under flow conditions. The arrow indicates the direction of initial precipitation.
Figure 7:
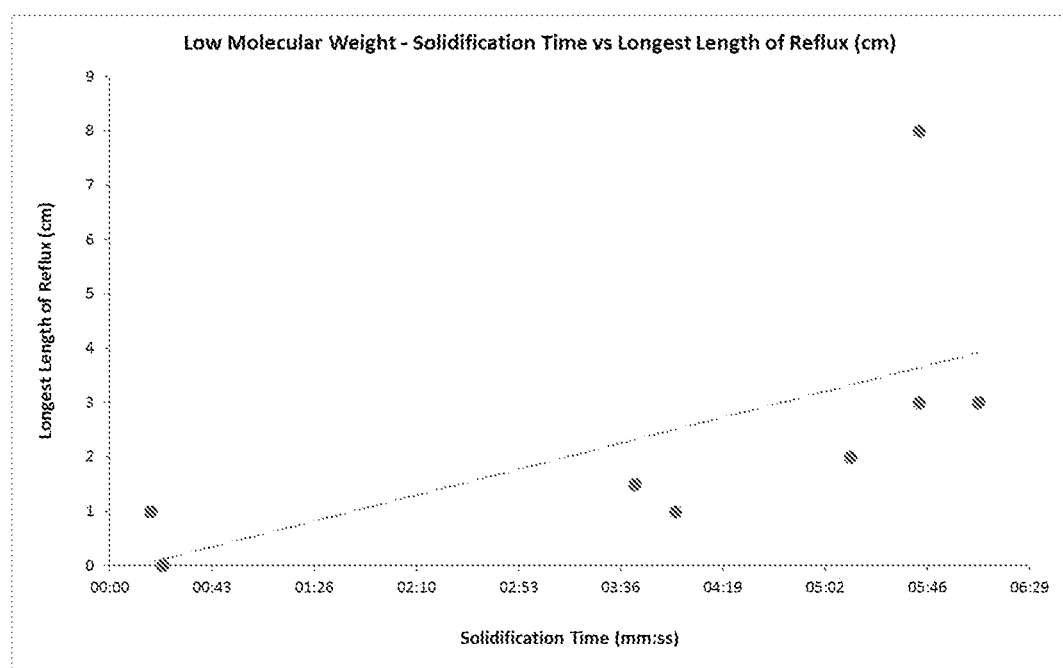
FIG. 7 is a graph showing the relationship between solidification time and reflux of the embolus in test conditions.

Table 3 illustrates precipitation fill volume changes with polymer concentration. FIG. 4 illustrates the effect of polymer concentration on fill volume

TABLE 3

| Sample Number | Radiopaque Group (TIBA) Equivalent | Polymer Concentration in DMSO (%) | Change in Fill Volume (%) |
|---|---|---|---|
| 1 | 0.25 | 8 | −77 |
| 2 | 0.25 | 20 | −46 |
| 3 | 0.20 | 20 | −33 |
| 4 | 0.40 | 4 | −85 |
| 5 | 0.40 | 8 | −58 |
| 6 | 0.40 | 12 | −84 |
| 7 | 0.40 | 16 | −31 |
| 8 | 0.60 | 4 | −99 |
| 9 | 0.60 | 8 | −57 |
| 10 | 0.60 | 12 | −40 |
| 11 | 0.60 | 16 | −40 |

Example 5: Particulate Generation

Particulate generation is a measure of the cohesiveness and stability of liquid embolic precipitates.

A syringe without a needle was used to deposit 0.5 mL of liquid embolic preparation, dropwise, into 30±5 ml of PBS in a 50 mL Duran bottle. The syringe was positioned at a height of 12 cm from the surface of the PBS. The liquid embolic was allowed to solidify for 10 minutes.

The Duran bottle was then capped and transferred to a plate shaker for 30 minutes at 240 rpm. The steps above were repeated with additional replicates of the liquid embolic sample to be tested and the plate shaker speed altered to 400 rpm and 640 rpm. The Duran bottles were removed from the plate shaker and samples allowed to settle. Visual inspection of the Duran bottles by eye was carried out to establish whether any large fragments of the precipitates had come away from the main precipitate during shaking and photographic images captured. Using a plastic pipette (with the tip cut off) an aliquot of solution from each Duran bottle was transferred to a Petri dish and assessed under light microscopy. Examples of particulates and fragments are shown in FIG. 3. The images obtained were assessed and given a score from 1-5 based on the amount of particulates generated and fragmentation observed. A score of 1 indicates a minimal degree of particulate generation and fragmentation while 5 indicates a high degree of particulate generation.

Table 4 illustrates the particle generation scores for low molecular weight polymers.

TABLE 4

| Sample Number | Radiopaque Group (TIBA) Equivalent | Polymer Concentration in DMSO (%) | Particle Generation Score |
|---|---|---|---|
| 2 | 0.25 | 20 | 4 |
| 3 | 0.20 | 20 | 1 |
| 4 | 0.40 | 4 | 5 |
| 5 | 0.40 | 8 | 1 |
| 6 | 0.40 | 12 | 2 |
| 7 | 0.40 | 16 | 1 |
| 9 | 0.60 | 8 | 2 |
| 10 | 0.60 | 12 | 1 |
| 11 | 0.60 | 16 | 1 |

Example 6: Precipitation Under Flow Conditions

A clear detachable tube was attached to a flow system through which PBS was pumped through the detachable tubing using a peristaltic pump to mimic blood flow conditions. A 2.4 Fr catheter was used to deliver the liquid embolic preparation into the detachable tube. As the liquid embolic left the catheter and came into contact with PBS, it precipitated inside the detachable tubing. The length of any precipitate was then measured from the end of the catheter tip. Flow rate and rate reduction were also recorded. The "longest length of advancement" was recorded. If reflux had occurred, its length was also recorded as the "longest length of reflux" (cm). The catheter was removed from the tubing of the precipitation testing equipment, and the ease of removal recorded.

Table 5 records precipitation properties of liquid embolic preparations

TABLE 5

| Sample Number | Radiopaque Group (TIBA) Equivalent | Polymer Conc. in DMSO (%) | Total Injection Volume (ml) | Longest Length of Reflux (cm) | Flowrate Reduction (%) | Catheter Withdrawal |
|---|---|---|---|---|---|---|
| 4 | 0.40 | 4 | 1.00 | 1.0 | 98 | OK |
| 5 | 0.40 | 8 | 0.60 | 1.5 | 98 | OK |
| 6 | 0.40 | 12 | 0.50 | 2.0 | 98 | OK |
| 7 | 0.40 | 16 | 0.65 | 3.0 | 99 | OK |
| 8 | 0.60 | 4 | 1.00 | Plug could not be achieved | | |
| 9 | 0.60 | 8 | 0.90 | 1.0 | 98 | OK |
| 10 | 0.60 | 12 | 0.65 | 8.0 | 99 | Stuck |
| 11 | 0.60 | 16 | 0.60 | 3.0 | 99 | OK |

Example 7: Measurement of Radiopacity

In order to obtain radiopacity measurements for the material, 1 cm sections of the precipitated formulation from Example 6 were cut and embedded in warm 1% agarose gel (prepared with Sigma-Aldrich product code A9539). The samples were prepared in Nunc cryotube vials (Sigma-Aldrich product code V7634, 48 mm×12.5 mm) and scanned using Micro-CT using a Bruker Skyscan 1172 Micro-CT scanner at the RSSL Laboratories, Reading, Berkshire, UK, fitted with a tungsten anode. Each sample was analysed using the same instrument configuration with a tungsten anode operating at a voltage of 64 kV and a current of 155 µA. An aluminium filter (500 µm) was used.

A summary of the acquisition parameters is given in Table 6.

TABLE 6

| Version 1.5 | |
|---|---|
| Software: | SkyScan1172 Version 1.5 (build 14) NRecon version 1.6.9.6 |
| CT Analyser version | 1.13.1.1 |
| Source Type: | 10 Mp Hamamatsu 100/250 |
| Camera Resolution (pixel): | 4000 × 2096 |
| Camera Binning: | 1 × 1 |
| Source Voltage | 65 kV |
| Source Current uA | 153 |
| Image Pixel Size (um): | 3.96 |
| Filter | Al 0.5 mm |
| Rotation Step (deg) | 0.280 |
| Output Format | 8 bit BMP |
| Dynamic Range | 0.000-0.140 |
| Smoothing | 0 |
| Beam Hardening | 0 |
| Post Alignment | corrected |
| Ring Artefacts | 16 |

Water (MilliQ®) blanks were scanned separately, prior to samples on the day of acquisition. Each sample was then analysed by X-Ray micro-computer. The samples may then be reconstructed using NRecon and calibrated against a volume of interest (VOI) of the purified water reference. A two part analysis method was used. Initially an interpolated region of interest is created coving the inner tube diameter to include the plug and any void structures then the image is segmented to isolate the polymer from the void structures. The radiodensity in HU was then calculated using the water standard acquired on the same day.

Table 8 shows the radiodensity values for liquid embolic preparations from Example 1, Table 1, prepared as 8% w/w solutions in DMSO and having varying levels of TIBA to PVA ratios. FIG. 8 shows microCT scans of precipitated liquid embolic polymers prepared with 0.10 (A) 0.15 (B) and 0.20 (C) eq. TIBA.

TABLE 8

| | Object | | | Total | |
|---|---|---|---|---|---|
| TIBA Eq. | Avg. grey scale value | Avg. HU | Obj Vol. (%) | Avg. grey scale value | Avg. HU |
| 0.25 | 66.64 | 3028.19 | 33.32 | 38.07 | 1301.57 |
| 0.4 | 81.59 | 3651.16 | 44.54 | 51.7 | 1947.08 |
| 0.6 | 93.19 | 4312.8 | 44.94 | 60.4 | 2443.26 |

The invention claimed is:

1. A liquid embolic composition suitable for therapeutic embolization, the composition comprising a polymer in solution in an organic solvent, the polymer comprising units of the formula 1:

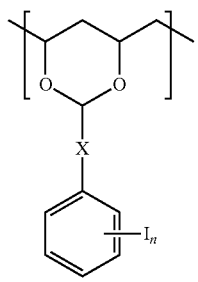

1 wherein X is either a bond or is a linking group having 1 to 8 carbons and optionally 1 to 4 heteroatoms selected from O, N and S;
wherein n is 1 to 4;
wherein the polymer precipitates on contact with normal saline at 20° C.;
wherein the precipitate has a radiodensity of at least 1000HU; and
wherein the polymer is biodegradable.

2. A liquid embolic composition according to claim 1 wherein n is 1, 2 or 3.

3. A liquid embolic composition according to claim 1 wherein the polymer comprises units selected from

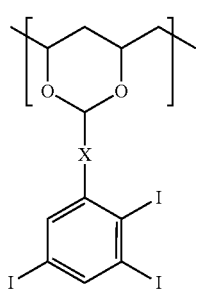

2a

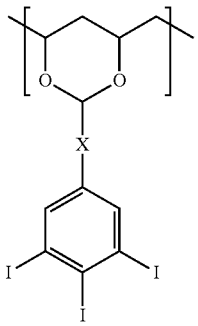

2b

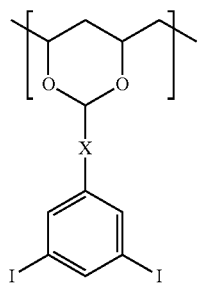

2c and

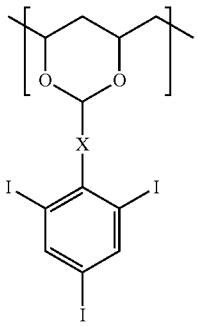

2d

4. A liquid embolic composition according to claim 1 where X is selected from a bond, $(C_{1-4})$alkylene, $(C_{1-4})$oxyalkylene and amino$(C_{1-4})$alkylene.

5. A liquid embolic composition according to claim 1 where X is a bond.

6. A liquid embolic composition according to claim 1 wherein the polymer comprises units of the formula 3

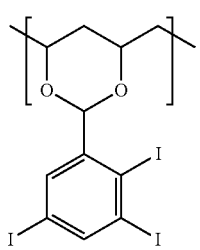

3

7. A liquid embolic composition according to claim 1 comprising the polymer and a water-miscible solvent.

8. A liquid embolic composition according to claim 7 comprising between 3% and 70% wt/wt of the polymer dissolved in the water-miscible solvent.

9. A liquid embolic composition according to claim 7 wherein the water-miscible solvent is a polar aprotic solvent.

10. A liquid embolic composition according to claim 7 wherein the water-miscible solvent is selected from dimethylsulphoxide, dimethylformamide, N, N'-dimethylpropyleneurea, 1,3-dimethyl-2-imidazolidinone, glycerol, ethyl lactate, N-Methyl-2-pyrrolidone and 2-(Oxolan-2-yl-methoxy)ethanol.

11. A liquid embolic composition according to claim 1 wherein n is 2 or 3.

12. A liquid embolic composition according to claim 1 wherein the polymer comprises a polyvinyl alcohol copolymer.

13. A liquid embolic composition according to claim 1 wherein the polymer is non cross linked.

14. A liquid embolic composition according to claim 1 wherein the polymer comprises iodine in an amount of 10% or greater (w/w) based on a dried weight of the polymer.

* * * * *